(12) United States Patent
Balboa

(10) Patent No.: US 10,893,858 B2
(45) Date of Patent: Jan. 19, 2021

(54) TAP-IN BONE ANCHOR WITH EXPANDING RING

(71) Applicant: Smith & Nephew, Inc., Memphis, TN (US)

(72) Inventor: Marc Joseph Balboa, Hopkinton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 158 days.

(21) Appl. No.: 16/094,387

(22) PCT Filed: Apr. 6, 2017

(86) PCT No.: PCT/US2017/026397
§ 371 (c)(1),
(2) Date: Oct. 17, 2018

(87) PCT Pub. No.: WO2017/189202
PCT Pub. Date: Nov. 2, 2017

(65) Prior Publication Data
US 2019/0125331 A1    May 2, 2019

Related U.S. Application Data

(60) Provisional application No. 62/327,588, filed on Apr. 26, 2016.

(51) Int. Cl.
*A61B 17/04* (2006.01)
(52) U.S. Cl.
CPC .... *A61B 17/0401* (2013.01); *A61B 2017/042* (2013.01); *A61B 2017/0403* (2013.01);
(Continued)

(58) Field of Classification Search
CPC ........ A61B 17/0401; A61B 2017/0403; A61B 2017/0412; A61B 2017/0414;
(Continued)

(56) References Cited

U.S. PATENT DOCUMENTS 5,501,695 A * 3/1996 Anspach, Jr. ...... A61B 17/0401
411/34
5,725,541 A * 3/1998 Anspach, III ...... A61B 17/0401
606/151

(Continued)

FOREIGN PATENT DOCUMENTS

| WO | 9838938 A1 | 9/1998 |
| WO | 2010105196 A1 | 9/2010 |
| WO | 2016155665 A1 | 10/2016 |

OTHER PUBLICATIONS

International Search Report and Written Opinion from related PCT Application No. PCT/US2017/026397 dated Jul. 11, 2017.

*Primary Examiner* — Shaun L David
(74) *Attorney, Agent, or Firm* — Burns & Levinson, LLP; Joseph M. Maraia

(57) ABSTRACT

An anchoring device for holding suture in bone includes an implant body with a proximal end and a distal end. A distal opening of the implant body is configured to receive a first proximal portion of an anchor. An expandable ring is initially press-fit about the first proximal portion of the anchor. The anchoring device is then located in a pre-drilled bore in a bone portion and the anchor portion is drawn proximally into the implant body, causing the ring to expand and contact the inner walls of the bone bore thus providing additional locking force of the anchoring device in the bone.

29 Claims, 4 Drawing Sheets

(52) U.S. Cl.
CPC ........... *A61B 2017/0412* (2013.01); *A61B 2017/0414* (2013.01); *A61B 2017/0432* (2013.01); *A61B 2017/0445* (2013.01)

(58) Field of Classification Search
CPC ...... A61B 2017/042; A61B 2017/0432; A61B 2017/0445
See application file for complete search history.

(56) References Cited

U.S. PATENT DOCUMENTS

| | | | | |
|---|---|---|---|---|
| 6,162,234 | A * | 12/2000 | Freedland | A61B 17/0401 |
| | | | | 411/344 |
| 2001/0053913 | A1* | 12/2001 | Freedland | A61F 2/0805 |
| | | | | 606/232 |
| 2005/0055027 | A1* | 3/2005 | Yeung | A61F 2/0811 |
| | | | | 606/75 |
| 2005/0113919 | A1* | 5/2005 | Cragg | A61F 2/4425 |
| | | | | 623/17.11 |
| 2010/0331881 | A1* | 12/2010 | Hart | A61B 17/0401 |
| | | | | 606/232 |
| 2015/0012095 | A1 | 1/2015 | Aeschlimann et al. | |
| 2015/0060599 | A1* | 3/2015 | Hakam | F21V 3/023 |
| | | | | 244/31 |
| 2015/0351815 | A1* | 12/2015 | Wales | A61B 17/7225 |
| | | | | 606/323 |
| 2016/0157849 | A1* | 6/2016 | Lunn | A61B 17/0401 |
| | | | | 606/232 |

* cited by examiner

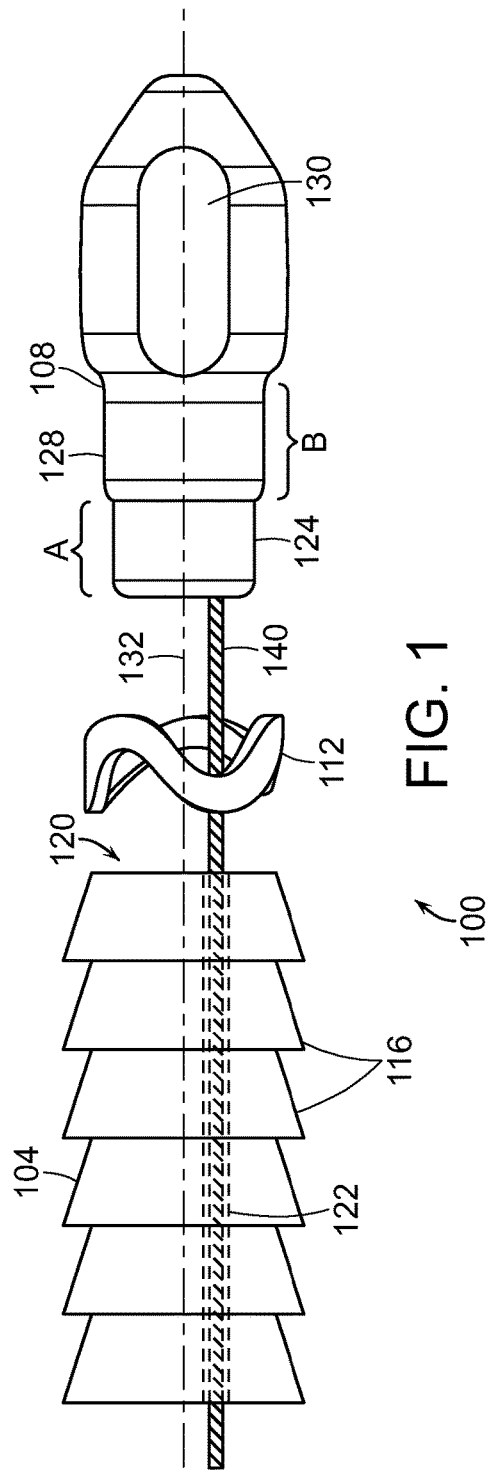
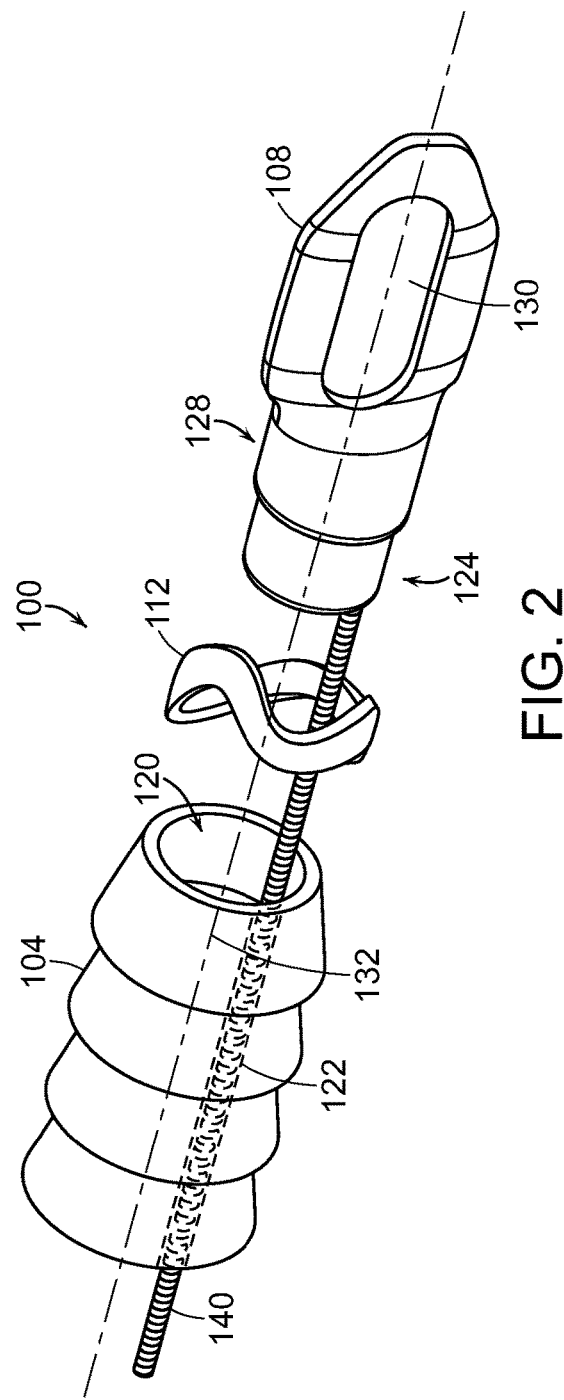

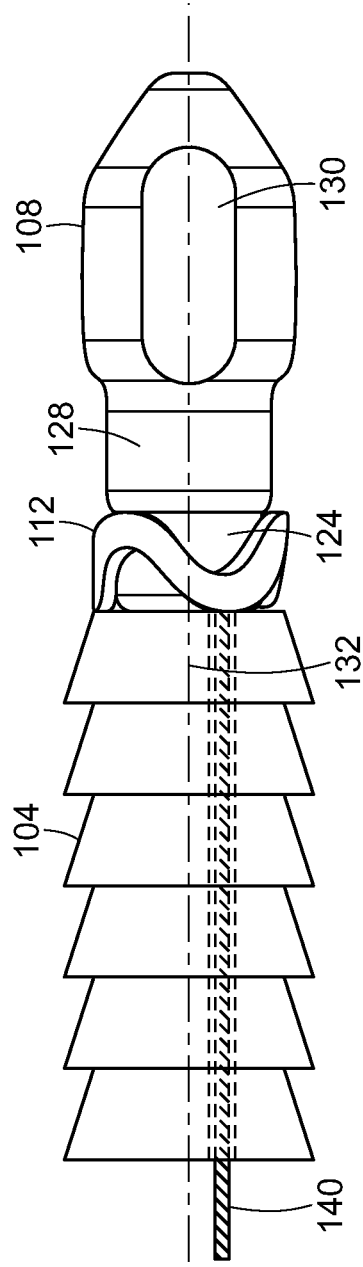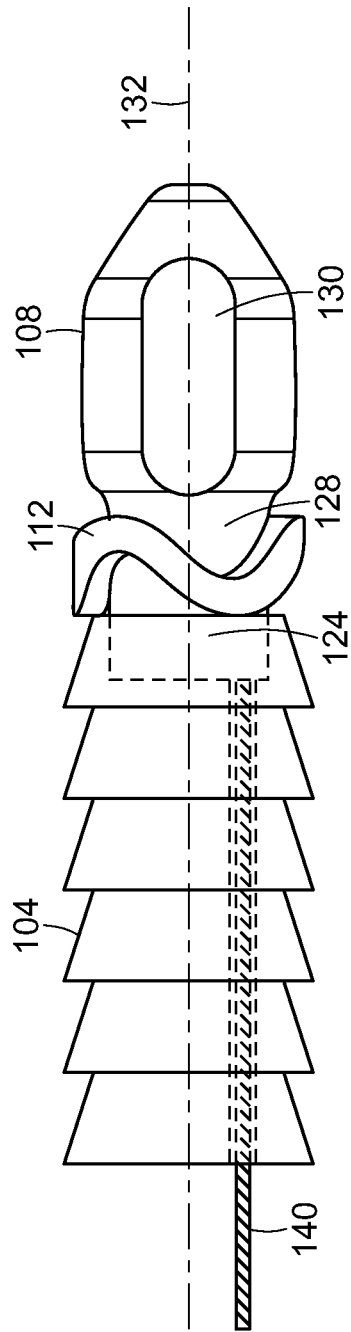
FIG. 3A
FIG. 3B

TAP-IN BONE ANCHOR WITH EXPANDING RING

CROSS REFERENCE TO RELATED APPLICATIONS

This application is the U.S. National Phase entry under 35 U.S.C. § 371 of International Application No. PCT/US2017/026397, filed Apr. 6, 2017, entitled TAP-IN BONE ANCHOR WITH EXPANDING RING, which claims priority to and the benefit of U.S. Provisional Application No. 62/327,588, filed Apr. 26, 2016, entitled TAP-IN BONE ANCHOR WITH EXPANDING RING.

BACKGROUND OF THE INVENTION

Known tap-in bone anchors tend to have lower fixation strengths than their screw-in counterparts. As a result, additional fixation mechanisms are necessary and the use of an expanding member is a common approach used to provide the additional fixation strength. Currently, in order to increase fixation in the bone, one approach to creating the additional contact pressure between the anchor and the bone utilizes some version of an expandable "wing." These methods are limiting in that they do not typically provide full circumferential expansion and, therefore, do not aid in locking the suture in a knotless construct.

What is needed is a tap-in bone anchor that has a fixation strength similar to that of a screw-in type.

BRIEF SUMMARY OF THE INVENTION

In one embodiment, a suture anchoring device includes an implant body having a proximal end and a distal end with a distal opening of the implant body located at the distal end having an inner diameter of a first diameter value. An anchor, having a first proximal portion with an outer diameter not greater than the first diameter value and a second proximal portion distally positioned with respect to the first proximal portion, is included. The second proximal portion has an outer diameter of a second diameter value greater than the first diameter value and the anchor first proximal portion is positioned adjacent the implant body distal opening. A first expandable closed ring is disposed about the anchor first proximal portion.

In another embodiment, a method of fixing a suture anchor in a portion of bone includes placing the anchoring device in the bone portion and moving the anchor proximally into the implant body and positioning the first ring about the second proximal portion of the anchor.

BRIEF DESCRIPTION OF THE DRAWINGS

Various aspects of at least one embodiment per the present disclosure are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention. In the figures:

FIG. 1 is an anchoring device in accordance with one embodiment of the present invention;

FIG. 2 is a perspective view of the anchoring device shown in FIG. 1;

FIGS. 3A and 3B are views of the anchoring device of FIG. 1 in first and second operative configurations, respectively;

DETAILED DESCRIPTION

Figure 4A:
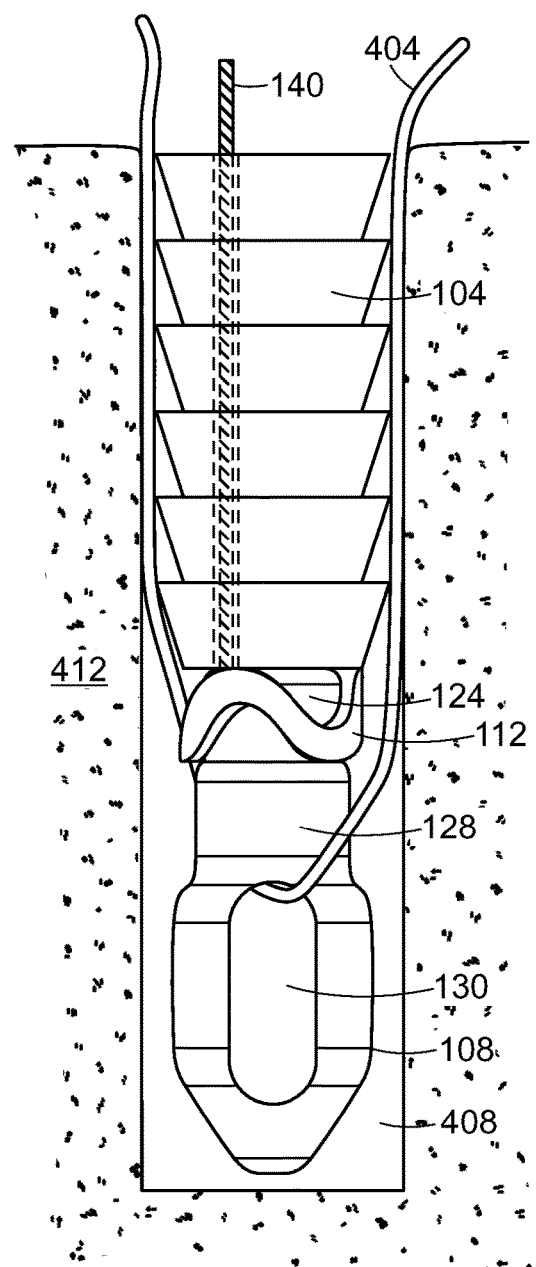
FIGS. 4A and 4B are views of the anchoring device of FIG. 1 in the first and second operative configurations in a bore in a portion of bone, respectively.

In the following detailed description, numerous specific details are set forth in order to provide a thorough understanding of the embodiments of the present disclosure. It will be understood by those of ordinary skill in the art that these embodiments may be practiced without some of these specific details. In other instances, well-known methods, procedures, components and structures may not have been described in detail so as not to obscure the embodiments of the present disclosure.

Prior to explaining at least one embodiment in detail, it is to be understood that the embodiment is not limited in its application to the details of construction and the arrangement of the components set forth in the following description or illustrated in the drawings. Other embodiments or other ways of being practiced or carried out are possible. Also, it is to be understood that the phraseology and terminology employed herein are for the purpose of description only and should not be regarded as limiting.

It is appreciated that certain features, are, for clarity, described in the context of separate embodiments but may also be provided in combination in a single embodiment. Conversely, various features are, for brevity, described in the context of a single embodiment but may also be provided separately or in any suitable sub-combination.

In the broadest sense, embodiments of the present disclosure are directed to a suture bone anchor that consists of multiple bodies and a ring. The combination of relative movements of the bodies causes expansion of the ring that then results in full circumferential expansion to aid in fixation and suture locking, as will be explained in more detail below.

Referring now to FIGS. 1 and 2, an anchoring device 100, in accordance with one embodiment, comprises an implant body 104, an anchor 108 and a ring 112. The implant body 104, in one embodiment, includes a plurality of barbs 116 on its outer surface and includes a distal opening 120 having an inner diameter of a first value at a distal end. The anchor 108 includes a first proximal portion 124 having an outer diameter not greater than the first value of the inner diameter of the distal opening 120 of the implant body 104. The body 104 includes a cannulation or bore 122 running through it that is configured to receive a positioning tool 140 that is releasably coupled to the anchor 108. In one embodiment, the bore 122 is offset from a central body axis 132 but, alternately, could be co-linearly located with the axis 132.

The tool 140 may be screwed into the anchor 108 such that it can be detached from the anchor 108. Of course, alternate mechanisms for releasably coupling could be implemented.

The anchor 108 also includes a second proximal portion 128 that is distally positioned with respect to the first proximal portion 124 and the second proximal portion 128 has an outer diameter of a second value that is greater than the first value. The anchor first proximal portion 124 has a corresponding length A and the anchor second proximal portion 128 has a corresponding length B. An eyelet 130 for receiving a portion of a suture is also defined in the anchor 108.

The ring 112 is closed and includes a plurality of undulations or oscillations and, therefore, results in a "wavy" configuration. The ring 112 has an inner diameter sized such that the ring 112 is in a slip-fit condition in an initial state with the anchor first proximal portion 124. The ring 112 is made from an expandable material.

In operation, the anchoring device 100 is arranged such that the ring 112 is disposed about the anchor first proximal portion 124 and the anchor first proximal portion 124 is then positioned adjacent to the distal opening 120 of the implant body 104 aligned along the axis 132, as shown in FIG. 1. The anchoring device 100, as arranged in FIG. 3A, is then provided with a suture 404 that has been threaded through the eyelet 130 and then placed in a bone bore 408 that has been provided in a portion of a bone 412, as shown in FIG. 4A. The implant body 104 remains stationary after insertion into the bone bore 408.

Figure 4B:
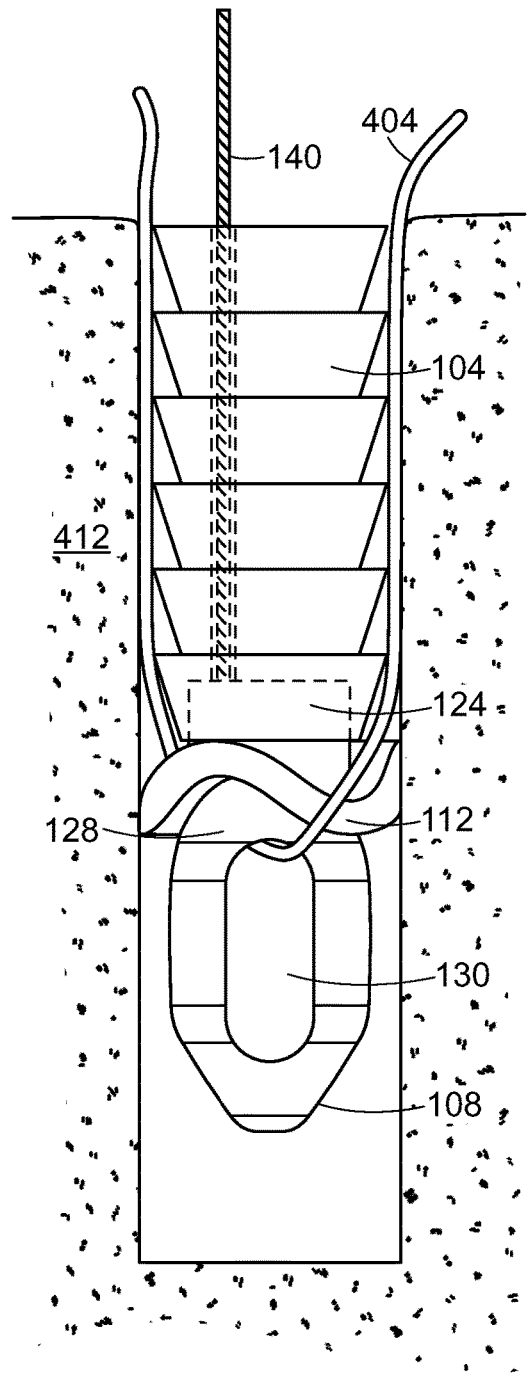

The anchor 108 is then retracted proximally into the implant body 104 by pulling the tool 140 and, consequently, the ring 112 expands and is press-fit onto the larger anchor second proximal portion 128, as shown in FIG. 4B and FIG. 3B. Advantageously, the implementation of the ring 112 provides full circumferential expansion to increase fixation strength without using "wings" that could possibly be sheared off during insertion or handling. Once expanded, the tool 140 is released from the anchor 108.

Figure 5:
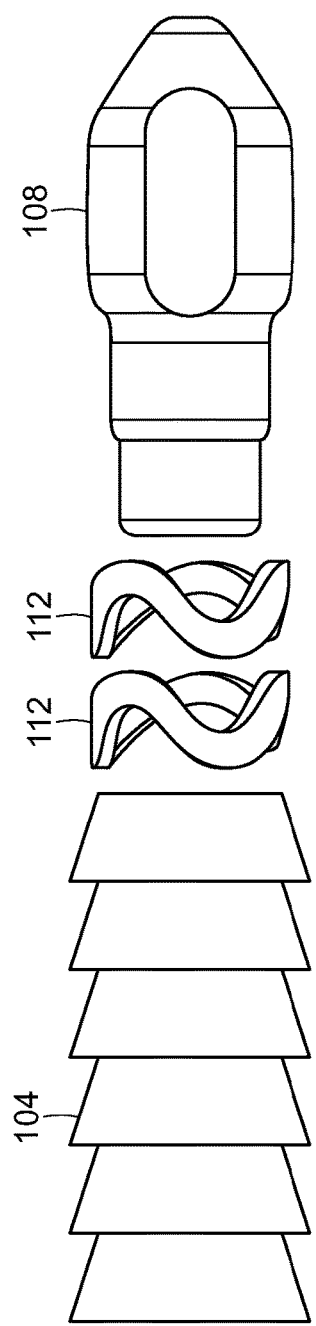
FIG. 5 is an anchoring device in accordance with another embodiment of the present invention.
Figure 6:
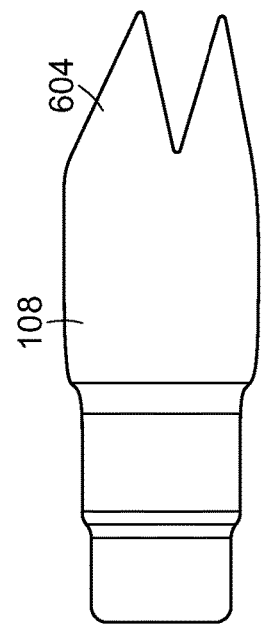
FIG. 6 is an anchor portion of the anchoring device in accordance with another embodiment of the present invention.

In one embodiment of the present invention, a plurality of rings 112 may be provided, as shown in FIG. 5. The design of the ring 112 may also vary as its wavelength, i.e., the number of oscillations, can be modified thereby reducing or increasing the amount of force required for expansion. In addition, the anchor 108 may comprise a fork, or a spear point 604, used to capture the suture 404 prior to implantation, as shown in FIG. 6. Of course, the anchor 108 may have both an eyelet 130 and a fork point 604 to provide alternate options for suture capture. The implant body 104 may utilize a tapered geometry where a proximal diameter is larger than a distal diameter, in an alternate embodiment. Further, the implant body 104 could implement fenestrations on its outer surface.

Figure 7:
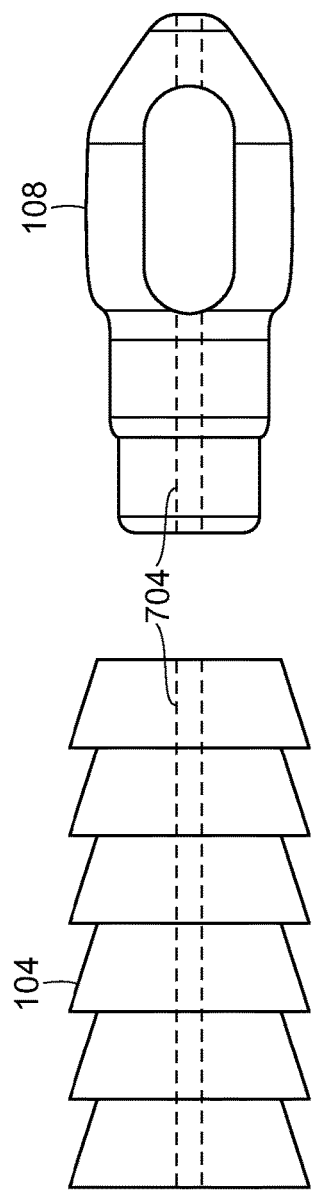
FIG. 7 is an anchoring device in accordance with yet another embodiment of the present invention.

Each of the implant body 104, the ring 112 and the anchor 108 could be made of any combination of metal, plastic, bioabsorbable, or biocomposite material. Still further, each of the implant body 104 and the anchor 108 may have an axial though-hole or conduit 704 running through them, and aligned, to be compatible with a guidewire (not shown) to aid in maintaining a correct trajectory and hole location for placement, as shown in FIG. 7. In addition, each of the implant body 104 and the anchor 108 could be sized such that the ring 112 can be forced more distally onto the anchor 108 in order to occlude or compress the eyelet 130, further preventing the suture 404 from sliding.

It is to be understood that the detailed descriptions of the embodiments of the present invention are provided by way of example only and are not intended to limit the scope of the invention. Features and/or steps described with respect to one embodiment may be used with other embodiments and not all embodiments of the invention have all of the features and/or steps shown in a particular figure or described with respect to one of the embodiments. Variations of embodiments described will occur to persons of skill in the art.

Although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the appended claims.

What is claimed is:

1. An anchoring device, comprising:
   an implant body having a central body axis, a proximal end and a distal end with a distal opening of the implant body located at the distal end of the implant body, the distal opening of the implant body having an inner diameter of a first diameter value;
   an anchor having a first proximal portion with an outer diameter not greater than the first diameter value and a second proximal portion distally positioned with respect to the first proximal portion, the second proximal portion having an outer diameter of a second diameter value greater than the first diameter value, the anchor first proximal portion positioned adjacent the implant body distal opening; and
   a first circumferentially expandable closed ring, disposed about the anchor first proximal portion, configured to circumferentially expand as the anchor is pulled into the implant body.

2. The anchoring device of claim 1, further comprising:
   a plurality of barbs extending from an outer surface of the implant body.

3. The anchoring device of claim 1, further comprising:
   a body conduit defined within the implant body and extending longitudinally about the central body axis.

4. The anchoring device of claim 3, further comprising:
   an anchor conduit running through the anchor extending longitudinally about an anchor central axis from a proximal end of the anchor to a distal end of the anchor, wherein the anchor central axis is co-linear with the central body axis.

5. The anchoring device of claim 1, wherein an eyelet is defined in a distal portion of the anchor.

6. The anchoring device of claim 1, wherein the first circumferentially expandable closed ring comprises a wave shape.

7. The anchoring device of claim 6, wherein the wave shape comprises a plurality of oscillations.

8. The anchoring device of claim 1, further comprising:
   a second circumferentially expandable closed ring disposed about the anchor first proximal portion and configured to circumferentially expand into a press-fit arrangement with the second proximal portion of the anchor when the anchor is pulled into the implant body.

9. The anchoring device of claim 1, further comprising:
   a fork disposed on a distal portion of the anchor.

10. The anchoring device of claim 1, wherein:
    the implant body comprises metal, plastic, bioabsorbable, biocomposite material, or any combination thereof.

11. The anchoring device of claim 1, wherein:
a length of the distal opening into the implant body is substantially equal to or greater than a length of the first proximal portion of the anchor.

12. The anchoring device of claim 1, further comprising:
a positioning tool disposed within the implant body and releasably coupled to the anchor.

13. The anchoring device of claim 1, wherein:
a length of the distal opening into the implant body is substantially equal to or greater than a sum of a length of the anchor first proximal portion and a length of the anchor second proximal portion.

14. The anchoring device of claim 1, wherein:
a length of the distal opening into the implant body is greater than a sum of a length of the anchor first proximal portion and a length of the anchor second proximal portion.

15. The anchoring device of claim 1, wherein the first circumferentially expandable closed ring is in a press-fit arrangement about the anchor first proximal portion.

16. The anchoring device of claim 1, wherein the first circumferentially expandable closed ring is configured to circumferentially expand to a diameter large enough to be positioned in a press-fit arrangement about the anchor second proximal portion.

17. The anchoring device of claim 1, wherein the first circumferentially expandable closed ring is configured to circumferentially expand to a diameter large enough to be positioned a distal portion of the anchor.

18. The anchoring device of claim 1, wherein:
the first circumferentially expandable closed ring is configured to circumferentially expand from a press-fit arrangement with the first proximal portion of the anchor to a press-fit arrangement with the second proximal portion of the anchor when the anchor is pulled into the implant body.

19. An anchoring device, comprising:
a barbed implant body, extending longitudinally about a central body axis, having a proximal end and a distal end, and a distal opening, the distal opening of the implant body having an inner diameter of a first diameter value;
an anchor, having a distal portion, a first proximal portion with an outer diameter not greater than the first diameter value and a second proximal portion distally positioned with respect to the first proximal portion of the anchor, the second proximal portion of the anchor having an outer diameter of a second diameter value greater than the first diameter value, the anchor first proximal portion positioned adjacent the implant body distal opening; and
a first circumferentially expandable closed ring disposed about the anchor first proximal portion and configured to circumferentially expand into a press-fit arrangement with the second proximal portion of the anchor.

20. The anchoring device of claim 19, wherein an eyelet is defined in the distal portion of the anchor.

21. The anchoring device of claim 19, further comprising a fork structure disposed on the distal portion of the anchor.

22. The anchoring device of claim 19, wherein the first circumferentially expandable closed ring comprises a wave shape.

23. The anchoring device of claim 22, wherein the wave shape comprises a plurality of oscillations.

24. The anchoring device of claim 19, further comprising:
a second circumferentially expandable closed ring disposed about the anchor first proximal portion and configured to circumferentially expand into a press-fit arrangement with the second proximal portion of the anchor.

25. The anchoring device of claim 19, wherein:
the barbed implant body comprises metal, plastic, bioabsorbable, biocomposite material, or any combination thereof.

26. The anchoring device of claim 19, further comprising:
a body conduit running through the barbed implant body and co-linear with the central body axis; and
an anchor conduit running through the anchor extending longitudinally about an anchor central axis from a proximal end of the anchor to a distal end of the anchor, wherein the anchor central axis is co-linear with the body conduit.

27. The anchoring device of claim 19, further comprising:
a positioning tool disposed within the implant body and releasably coupled to the anchor.

28. A suture anchoring device, comprising:
an anchor having a first proximal portion with an outer diameter of a first diameter value and a second proximal portion distally positioned with respect to the first proximal portion, the second proximal portion having an outer diameter of a second diameter value greater than the first diameter value;
an implant body having a central body axis, a proximal end and a distal end with a distal opening of the implant body located at the distal end of the implant body configured to receive the anchor first proximal portion, the implant body distal opening positioned adjacent the anchor first proximal portion; and
a first circumferentially expandable closed ring, disposed in a press-fit arrangement about the anchor first proximal portion, configured to circumferentially expand as the anchor is pulled into the implant body.

29. A method of fixing a suture anchor in a portion of bone, the method comprising:
providing the anchoring device as recited in claim 1;
positioning the anchoring device in the bone portion;
moving the anchor proximally into the implant body; and
positioning the first circumferentially expandable ring about the second proximal portion of the anchor.

* * * * *